United States Patent [19]
Duchesne et al.

[11] Patent Number: 5,359,124
[45] Date of Patent: Oct. 25, 1994

[54] β-PHENYLISOSERINE DERIVATIVE, ITS PREPARATION AND ITS USE

[76] Inventors: Jean-Pierre Duchesne, 160 rue Marcel Merieux, 69007 Lyon; Michel Mulhauser, Frenes 4, Residence Carriere Blanche, 69130 Ecully, both of France

[21] Appl. No.: 920,508

[22] PCT Filed: Feb. 20, 1991

[86] PCT No.: PCT/FR91/00132
§ 371 Date: Aug. 21, 1992
§ 102(e) Date: Aug. 21, 1992

[87] PCT Pub. No.: WO91/13053
PCT Pub. Date: Sep. 5, 1991

[30] Foreign Application Priority Data
Feb. 21, 1990 [FR] France .................. 90 02099

[51] Int. Cl.$^5$ .......................................... C07C 229/12
[52] U.S. Cl. ........................................ 560/40; 562/445
[58] Field of Search .................. 562/435, 444, 445; 560/40

[56] References Cited

U.S. PATENT DOCUMENTS
4,240,975 12/1980 Umezawa ........................ 562/437

FOREIGN PATENT DOCUMENTS
336840 10/1989 European Pat. Off. .
336841 10/1989 European Pat. Off. .
400971 12/1990 European Pat. Off. .

OTHER PUBLICATIONS

Chemical Abstract 91:20066h.
Journal of the Chemical Society, Chemical Communications, No. 18, 1988 Sunggak Kim, et al. "A convenient method for beta-lactam formation from beta-amino acids using diphenylphosphinic chloride", pp. 1242-1243 (see p. 1243).
Journal of Organic Chemistry, vol. 51, No. 1, 10 Jan. 1986, Denis et al. "An efficient, enantioselective synthesis of the taxol side chain", pp. 46-50 (see pp. 48-49, cited in the application).
Bulletin Korean Chemical Society, vol. 9, No. 3, Mar, 22, 1988, Sunggak Kim, et al., "A new method for beta ∝ lactam formation from beta-amino acids using benzotriazol-1-yloxytris (dimethylamino) phosphonium hexafluorophosphate", pp. 189-190 (see the whole document).
Archiv der Pharmazie, vol. 307, 1974, Kamandi et al., "Die synthese von beta-phenyloisoserinen durch ammonolyse von beta-phenylglycidestern, I", pp. 871-878, (see the whole document).
Journal of the American Chemical Society, vol. 110, No. 19, Sep. 14, 1988, Holton, et al., "A synthesis of taxusin", pp. 6558-6560.
Journal of the American Chemical Society, vol. 110, No. 17, Aug. 17, 1988, Denis, et al., "A highly efficient, practical approach to natural taxol", pp. 5917-5919 (see p. 5918).
Archiv der Pharmazie, vol. 308, 1975, Kamandi, et al., "Die synthese von beta-phenyl-isoserinen durch ammonolyse von beta-phenylhlycidestern II", pp. 135-141.

*Primary Examiner*—Jose G. Dees
*Assistant Examiner*—Samuel Barts

[57] ABSTRACT

New β-phenylisoserine derivative of formula (I), its preparation and its use as intermediate in the synthesis of taxol or of its derivatives.

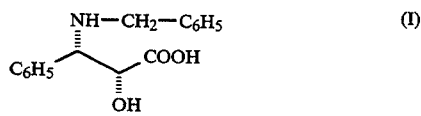

3 Claims, No Drawings

β-PHENYLISOSERINE DERIVATIVE, ITS PREPARATION AND ITS USE

FIELD OF THE INVENTION

The present invention relates to a new β-phenylisoserine derivative of formula:

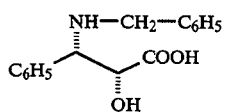

optionally in salt or ester form, to its preparation and to its use.

BACKGROUND OF THE INVENTION

According to E. Kamandi et al., Arch. Pharmaz., 307, 871-878 (1974), it is known to prepare threo-β-phenylisoserine by the action of ammonia on an ester of cis-β-phenylglycidic acid, followed by the action of barytes, in order to avoid racemisation, on the β-phenylisoserine amide obtained as an intermediate.

According to E. Kamandi et al., Arch. Pharmaz., 308, 135-141 (1975), the action of benzylamine on an ester of trans-β-phenylglycidic acid leads to the formation of erythro-N,N'-dibenzyl-β-phenylisoserine amide which, on hydrogenation in the presence of palladium on charcoal, leads to erythro-β-phenylisoserine-N-benzylamide.

DESCRIPTION OF THE INVENTION

According to the invention, the product of formula (I) can be obtained by the action of benzylamine on (2R,3R)-cis-β-phenylglycidic acid, preferably in the form of an alkali metal salt such as the potassium salt or a salt with a nitrogenous base such as benzylamine, the operation being carried out in water at a temperature which is generally between 40° and 100° C.

1 to 40 moles of benzylamine are generally employed per mole of cis-β-phenylglycidic acid.

The product of formula (I), preferably in the form of an alkali metal salt such as the potassium salt, or in the form of a salt with a nitrogenous base such as benzylamine, is obtained after concentrating to dryness the solution obtained.

The product of formula (I) thus obtained can be converted into a (2R,3S)-β-phenylisoserine ester by the action of an alcohol in acidic medium, followed by catalytic hydrogenation, preferably in the presence of palladium on charcoal.

The (2R,3S)-β-phenylisoserine ester is particularly useful for preparing the taxane derivatives of general formula:

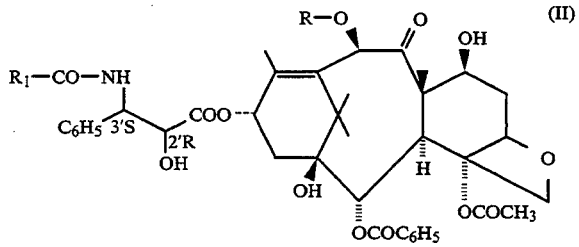

in which R denotes a hydrogen atom or an acetyl radical and R₁ denotes a phenyl or t-butoxy radical, according to the process described in European Patent Applications EP 0,336,840 or EP 0,336,841.

(2R,3R)-cis-β-Phenylglycidic acid can be prepared under the conditions described by J-N. Denis et al., J. Org. Chem., 51, 46-50 (1986).

The present invention also relates to the product of general formula (II) when it is obtained by a process using the product of formula (I).

The present invention also relates to the pharmaceutical compositions containing a product of general formula (II) when it is obtained by a process using the product of formula (I), in combination with any other pharmaceutically acceptable product, be it inert or physiologically active.

These compositions may be presented in any form which is appropriate to the intended route of administration. The parenteral route is the preferred route of administration, and especially the intravenous route.

The compositions for parenteral administration may be aqueous or nonaqueous sterile solutions, suspensions or emulsions. The solvent or carrier employed may be propylene glycol, vegetable oils, in particular olive oil, and injectable organic esters, for example ethyl oleate. These compositions may also include adjuvants, in particular wetting, emulsifying or dispersing agents. The sterilization may be performed in a number of ways, for example with the aid of a bacteriological filter, by incorporating sterilizing agents in the composition, by irradiation or by heating. They may also be in the form of sterile compositions which may be dissolved or dispersed in sterile water or any other injectable sterile medium.

These compositions are particularly useful in the treatment of acute leukaemia and of solid tumors.

EXAMPLES

The following examples, given without any limitation being implied, show how the invention can be put into practice.

EXAMPLE 1

18.2 g of potassium salt of (2R,3R)-cis-β-phenylglycidic acid (0.09 moles), 65 cm³ of water and 180 cm³ of benzylamine are introduced into a reactor. The mixture is heated to 50° C. for 4 hours 30 minutes. After cooling, the reaction mixture is extracted with 2×200 cm³ of dichloromethane. The aqueous phase is concentrated to dryness. 24.2 g of potassium salt of (2R,3S)-N-benzyl-β-phenylisoserine are thus obtained; its rotatory power is $[\alpha]_D^{20} = +38.4°$ (c=3.6, water).

The structure of the product is confirmed by infrared, mass and nuclear magnetic resonance spectra.

EXAMPLE 2

23.2 g of the salt obtained in Example 1 (0.075 moles) and 260 cm³ of methanol are introduced into a reactor. The solution is saturated with dry gaseous hydrochloric acid. After 3 hours' stirring at a temperature close to 20° C. the potassium chloride which has precipitated out is separated off by filtration. The solution is concentrated to dryness and the residue is washed with acetone and then filtered off. The product obtained (28.84 g) is dissolved in 80 cm³ of methanol. 7 g of palladium on charcoal are added. The reaction mixture is placed under a hydrogen atmosphere. After several hours' stirring at a temperature close to 20° C., the hydrogen absorption is finished. After filtering and concentrating the filtrate, 13.5 g of hydrochloride of the methyl ester of (2R,3S)-β-phenylisoserine are obtained; its rotatory power is $[\alpha]_D^{20} = -18.5°$ (C=1.2, water).

EXAMPLE 3

143 g of the salt of (2R,3R)-cis-β-phenylglycidic acid with α-methylbenzylamine (0.5 moles) are introduced into a reactor containing 1 liter of dichloromethane. The suspension is cooled to 15° C. and a solution of 33 g of 85% potassium hydroxide (0.5 moles) in 100 cm³ of water is then added over 10 minutes.

The aqueous phase is separated off and the organic phase is then extracted with 50 cm³ of water.

The combined aqueous phases are washed with 100 cm³ of methylene chloride.

The aqueous solution of the potassium salt is introduced into a reactor with 54 g of benzylamine (0.5 moles). The mixture is heated to 80° C. for 2 hours. After cooling over 2 hours to a temperature close to 20° C. the reaction mixture is poured into 3 liters of iced water. 170 cm³ of a 1.5M solution of sulphuric acid are added; the pH is then 7.7. The product which precipitates out is separated off by filtration, is washed with 3×600 cm³ of water and 300 cm³ of acetone. After drying, 100.6 g of (2R,3S)-N-benzyl-β-phenylisoserine are obtained.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. β-Phenylisoserine derivative of formula:

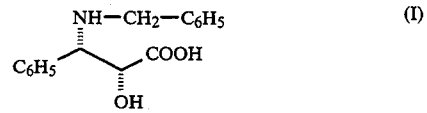

optionally in the form of an alkali metal salt or a salt with a nitrogenous base or a methyl ester.

2. Process for the preparation of the product according to claim 1, comprising reacting benzylamine with (2R,3R)-cis-β-phenylglycidic acid, carrying out the operation in water, and isolating the product obtained and converting that product into an alkali metal salt or a salt with a nitrogenous base or a methyl ester.

3. Method for preparing (2R,3S)-β-phenylisoserine ester comprising reacting the alkali metal salt of claim 1 with an alcohol in acidic medium to provide a reaction mixture, adding a catalyst to the reaction mixture and placing the reaction mixture under a hydrogen atmosphere, whereby an ester of (2R,3S)-β-phenylisoserine is obtained.

* * * * *